United States Patent [19]

Freund et al.

[11] Patent Number: 4,558,752

[45] Date of Patent: Dec. 17, 1985

[54] DEVICE FOR OBTAINING DUST FROM MINERALS

[75] Inventors: Hans-Ulrich Freund, Friedrichsdorf; Wolfgang M. Heide, Darmstadt; Rolf A. Sieglen, Sulzbach, all of Fed. Rep. of Germany

[73] Assignee: Luossavaara Kiirunavaara AB, Stockholm, Sweden

[21] Appl. No.: 212,729

[22] PCT Filed: Feb. 22, 1980

[86] PCT No.: PCT/EP80/00011

§ 371 Date: Oct. 27, 1980

§ 102(e) Date: Oct. 27, 1980

[87] PCT Pub. No.: WO80/01838

PCT Pub. Date: Sep. 4, 1980

[30] Foreign Application Priority Data

Feb. 26, 1979 [DE] Fed. Rep. of Germany ....... 2907514

[51] Int. Cl.[4] .................... E21C 39/00; E21C 37/26; E21C 37/20
[52] U.S. Cl. .................................. 175/207; 175/213; 299/14; 73/864.41
[58] Field of Search .................. 175/55, 56, 66, 71, 175/206, 14, 18, 213; 299/14, 18; 73/864.41; 83/919; 125/6, 29, 30 R; 310/26; 51/595 S

[56] References Cited

U.S. PATENT DOCUMENTS

| | | | |
|---|---|---|---|
| 2,651,148 | 9/1953 | Carwile | 310/26 X |
| 2,831,668 | 4/1958 | Skowronski | 175/56 X |
| 2,834,158 | 5/1958 | Petermann | 310/26 X |
| 3,144,912 | 8/1964 | Boehm et al. | 175/213 |
| 3,419,776 | 12/1968 | Kleesattel et al. | 310/26 X |
| 3,442,337 | 5/1969 | Astrom | 175/213 X |
| 3,460,637 | 8/1969 | Schulin | 175/56 |
| 3,511,323 | 5/1970 | Riley | 175/56 X |
| 3,526,219 | 9/1970 | Balamuth | 175/56 X |
| 3,528,514 | 9/1970 | Sandvig | 175/206 X |
| 3,589,352 | 6/1971 | Carlsson et al. | 175/213 X |
| 3,735,824 | 5/1973 | Astrom | 175/213 |
| 3,843,198 | 10/1974 | Reynolds | 299/18 |

FOREIGN PATENT DOCUMENTS

| | | |
|---|---|---|
| 980144 | 12/1975 | Canada . |
| 2310663 | 10/1974 | Fed. Rep. of Germany . |
| 1554504 | 1/1969 | France . |
| 542695 | 11/1973 | Switzerland . |
| 735969 | 8/1955 | United Kingdom . |
| 788052 | 12/1957 | United Kingdom . |
| 1113555 | 5/1968 | United Kingdom . |
| 565226 | 7/1977 | U.S.S.R. ............ 73/864.41 |

Primary Examiner—Stephen J. Novosad
Assistant Examiner—M. Goodwin
Attorney, Agent, or Firm—Fisher, Christen & Sabol

[57] ABSTRACT

Device for obtaining dust from minerals. The device has an excitation part for mechanical ultrasonic vibrations combined with a chisel. A suction device is provided to collect the dust produced. The device serves in particular to produce dust samples rapidly for quick analysis of minerals in prospecting, in the reconnaissance and evaluation of deposits and in the mining of minerals for the purposes of quality control, monitoring and controlling the mining process.

13 Claims, 13 Drawing Figures

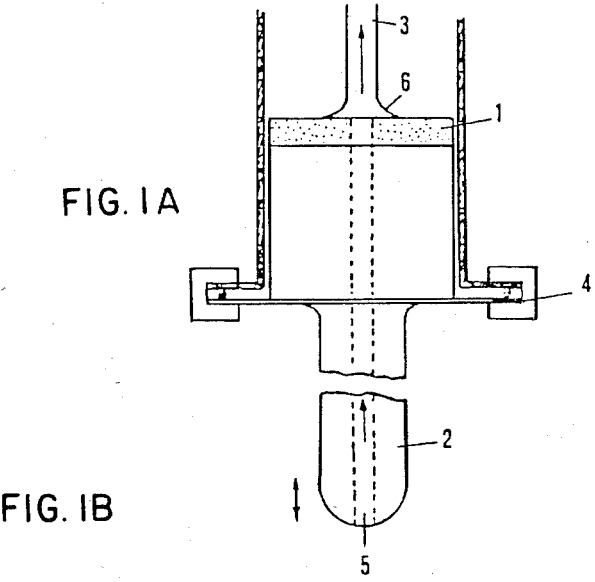
FIG. IA
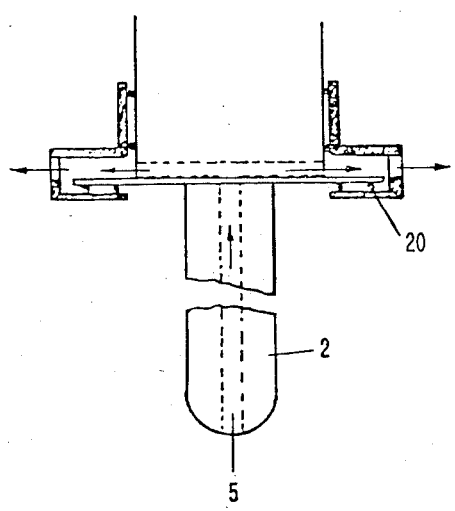
FIG. IB
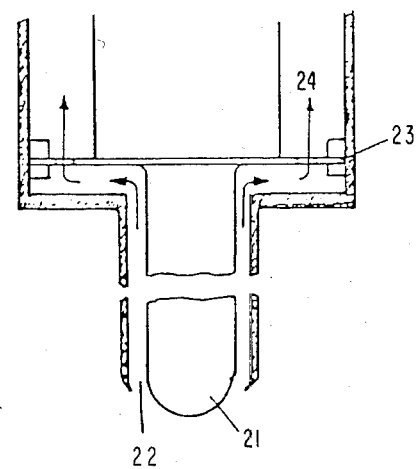
FIG. IC

DEVICE FOR OBTAINING DUST FROM MINERALS

BACKGROUND OF THIS INVENTION

1. Field of this Invention

This invention relates to devices for obtaining dust from minerals.

2. Prior Art

At present, prospectors collect above-ground mineral samples on the basis of geological, mineralogical and other indicators. Chunks of mineral for this purpose are separated from the solid rock or from larger chunks using simple tools. The lumps of ore are morphologically analyzed and subjected to chemical elemental analysis. Bore hole ground samples or bore hole cores are drawn in the prospecting of underground deposits. Likewise the ground material, which is obtained during drilling and transported from the bore hole by means of flushing means, may also be used for the purpose of analysis. In both cases, fairly large quantities of up to a few kilograms of starting material are needed, the starting material is then possibly ground, dried and homogenised. A small representative fraction of this is used for the analysis.

In the mining of mineral raw materials, samples are taken from the mineral transport flow at various points, beginning at the working point. Taking a reliable, representative sample is important for quality control. This means that a large initial quantity of material of a few hundred kilogram is required for each analysis, which is taken from the conveyor belt, truck load or stockpile. This initial quantity may possibly be processed further in several stages always in separated fractions, for example, dried, crushed, etc. At the end of this process there is also a small quantity of a few grams of substance which is used in the analysis a relatively small amount in comparison to the initial quantity.

The elemental analysis is conducted, for example, by the wet-chemical method or by using X-ray fluorescence. In the first process the sample-substance is dissolved in strong acids and then subjected to quantitative testing methods which are adapted to the elemental components of the valuable mineral in question. These processes include simple robust methods for use in field work and complex methods using automated apparatus for use in the laboratory. In the case of X-ray fluorescence, the sample material is pressed into pellets and fed into an automated analytical instrument. The sample may be analysed for elements with atomic numbers greater than ten, with a certain detection limit specific for the element.

DESCRIPTION OF THIS INVENTION

The present invention is based on the task of developing a device with which representative sample material may be obtained within a very short period of time. In particular, the sample should be of small grain size and be suitable for direct analysis.

It has been found that this problem can be solved in a technically progressive manner if the device consists of an excitation part for mechanical ultrasonic vibrations coupled with a chisel, and if a suction device is provided to collect the dust produced.

The device serves in particular to produce dust samples rapidly for quick analysis of minerals in prospecting, in the reconnaissance and evaluation of deposits and in the mining of minerals for the purposes of quality control, monitoring and controlling the mining process.

Advantageously, in the device, the chisel is pivoted, and the chisel tip is calotte-shaped, conical or bevelled. Advantageously, the suction nozzle concentrically surrounds the chisel tip. Advantageously, the chisel tip contains a bore hole which represents the suction nozzle of the suction device. Further advantageously, a filter is provided in the air flow of the suction device to collect the dust produced. Advantageously, an impactor is used in the suction device to collect the dust produced.

The ultrasonic excitation part supplies the energy for exciting the chisel to high-frequency mechanical vibrations. Piezoelectric or magnetostrictive transducers may be used for this purpose. The chisel is coupled with the excitation part and vibrates with maximum amplitude at the tip. The chisel tip is shaped so as to favor the production of dust and so as to make a maximum quantity of dust accessible to the suction device. Depending on the nature of the mineral to be investigated, the chisel tip may be calotte-shaped, conical or bevelled. If necessary, the chisel may also rotate.

The material from which the chisel is made must have a good fatigue strength and low inside losses. Various metals are suitable for this, especially alloys of titanium. The chisel tip may also be protected against abrasion. This may be done by applying a special working material, such as, metal-ceramic materials, by incorporation of, for example, ceramic abrasive particles, or by surface treatment, e.g., nitriding or carburation. The chisel may also be made completely from a homogeneous, abrasive-resistant, powder metallurgical sintered material.

The suction device consists of the suction head, the suction line and the dust collecting part. The suction nozzle can be close to the chisel tip without touching it. The nozzle may also concentrically surround the chisel tip. Furthermore, the chisel tip may contain a bore hole which forms the suction nozzle. The dust collecting part is usually a filter head for membrane filters. But an impactor in the suction pipe may also be used to collect the dust produced. A pump and control unit serves to control the air throughput.

In the following more details are given about this invention on the basis of the drawings. In the drawings, which are in a simplified, schematic form:

FIGS. 1A to 1C show, in partially cross-sectional, front elevational views, three embodiments of the device according to this invention.

Figures 2A, 2E:
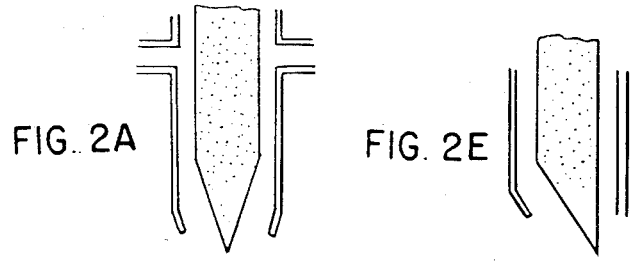
FIGS. 2A to 2G show, in partially cross-sectional, front elevational view, several shapes of the chisel tip.
Figures 2B, 2F:
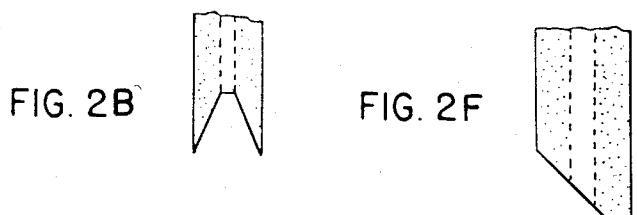
Figures 2C, 2G:
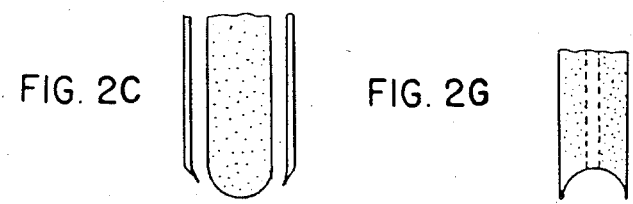
Figure 2D:
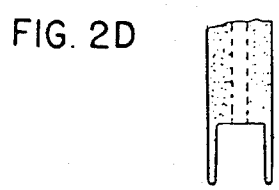

As FIG. 1A shows, the device according to this invention consists of excitation part 1, chisel 2 and a suction device with suction line 3. In order to raise the amplitude of the vibration of chisel 2, the cross section of chisel 2 is reduced in comparison to the cross section of excitation system 1. The device is mechanically fixed in the nodal plane $\lambda/4$ by a nodal mounting 4. Chisel 2 is affixed to the nodal plate which is affixed to nodal mounting 4.

The suction device consists of suction nozzle 5, the suction line 3 and the dust collecting part. The latter unit is not shown in the diagram, nor is the pump and control unit for controlling the volume of the air throughput. Suction nozzle 5 or a part of suction line 3 may be formed by an axial bore drilled by chisel 2, as shown diagrammatically in FIGS. 1A and 1B. According to the embodiment shown in FIG. 1A the bore hole, which forms part of suction line 3, also passes through excitation system 1. In this case part 6 of suction line 3 which forms the point of connection with excitation system 1 would have to be made from an elastic material so as not to impair the vibrations of excitation system 1. In the embodiment shown in FIG. 1B the sucked-in material is not guided centrally through excitation system 1, but is guided radially in the area of the vibration node to a joint exit. Chisel 2 is affixed to the nodal plate which is affixed to nodal mounting 20.

In the embodiment shown in FIG. 1C, suction nozzle 22 surrounds the chisel tip 2 concentrically. Chisel 21 is affixed to the nodal plate which is affixed to nodal mounting 23. The nodal plate contains holes 29. In this case, too, various possibilities for leading off the dust produced are also conceivable. The suction duct 24 may be guided either in a radial direction or in an axial direction. The dust produced is passed through the suction duct to a dust collecting part. This dust collecting part consists of either a filter head or an impactor for larger quantities of dust. This method of collecting sample material also permits continuous removal.

FIGS. 2A to 2G show several shapes of the chisel tip. Other possible shapes are also conceivable. In the embodiments in FIGS. 2A, 2C and 2E the dust is drawn off concentrically around the chisel tip, while in FIGS. 2B, 2D, 2F and 2G suction occurs through the tip of the chisel.

Figure 5:
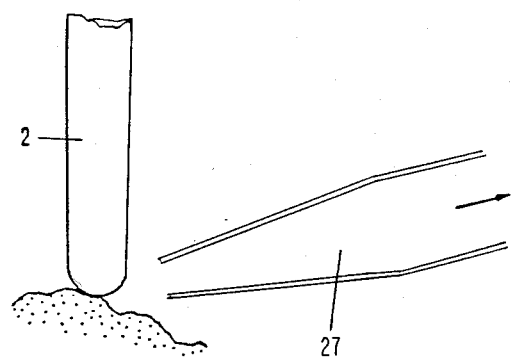
FIG. 5 is a diagram showing the chisel according to this invention with a separate suction device.
Figure 3:
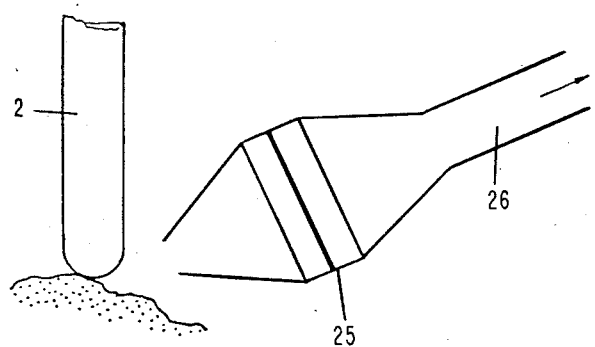
FIG. 3 shows two partially cross-sectional, front elevational views of the chisel according to this invention with separate suction device.

However the dust may also be drawn off directly beside the chisel tip, as shown in FIG. 3. In this case, the suction line 26 is brought up close to chisel tip 2 at an inclination, without touching the tip. Filter head 25 may also be near the suction nozzle. This version has the advantage that practically no cleaning of the suction pipe of dust deposits is necessary. FIG. 5 shows a similar embodiment wherein numeral 27 represents the separate suction line.

Figure 4:
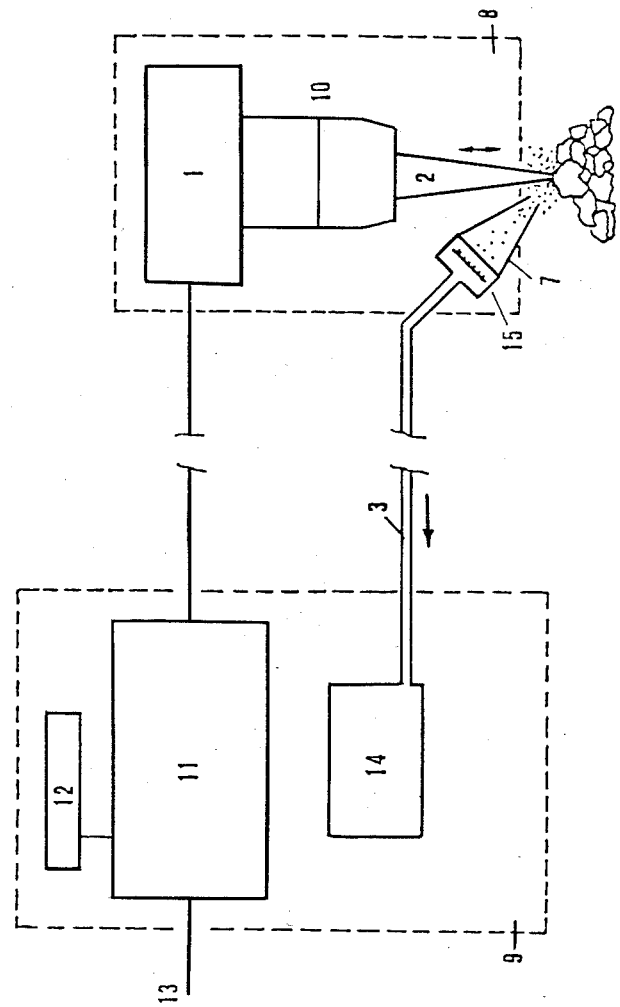
FIG. 4 is a diagram of the device according to this invention.

From the diagram of an embodiment according to the invention, shown in FIG. 4, it is clear that the device comprises basically two units, namely, hand operated device 8 and portable unit 9. Hand operated device 8 consists of excitation part 1, the ultrasonic coupler 10 and chisel 2. Portable unit 9 contains control unit 11 with battery 12, or mains connection 13, a suction pump 14 and suction line 3. Filter sample 15 is collected by filter head 7.

Using the device according to this invention, dust with very fine particle size is produced from the surface of chunks of mineral or from solid rock. The high efficiency range of the particle size is from a few to about 100 $\mu$m diameter. The composition of the dust is identical to that of the mineral at the point where the ultrasonic chisel touches the surface. In those cases where several relatively small areas of a mineral vein or a fairly large area of it is desired, the ultrasonic chisel may be successively positioned at the desired points. Especially for large-area or large-volume sampling, parallel individual devices may be fixed to a joint mounting. The cloud of dust which is produced in a small area around the chisel tip is drawn off into the dust collecting part. Thus it is possible to produce and collect dust from dry and moist minerals. By drawing them onto a membrane filter, the dust samples may be rendered into a form in which they may be fed directly to an energy dispersive X-ray fluorescence analysis (EDX).

Using the device according to this invention it is possible to produce a sample within a very short time, for example, 10 sec., due to the effective dust production and the small quantity of substance required for the sample. In this way a large number of samples per unit of time may be obtained. In addition, the sample material is crushed to a very small particle size of about 10 to 100 $\mu$m directly at the tip of the chisel. Whenever required or effective a fraction of the sample material is obtained in order, for example, to facilitate the subsequent analysis. This may be achieved with the help of a filter or impactor insertion into the suction line. The samples collected reflect the element composition of the mineral at the point where the chisel was applied. Contamination by surrounding material is impossible.

The device according to this invention for the production and collection of dust from minerals may be designed as a battery-operated portable unit. This permits convenient prospecting of remote deposits. Samples in the form of homogenously coated dust filter samples may then be analyzed directly in, for example, a mobile EDX field device.

What is claimed is:

1. Device for obtaining samples from minerals during the mining comprising an excitation part for mechanical ultrasonic vibrations combined with a chisel, which has a tip, and a suction device, the chisel being able to produce only dust of particle size of about 10 to 100 $\mu$m as sample for X-ray fluorescence analysis as a result of the reduction of the cross-section of the chisel in comparison to the cross-section of the excitation system and mechanically fixing the device in the nodal plane $\lambda/4$ by a nodal mounting and the suction device having a suction nozzle to collect the dust sample produced.

2. Device as claimed in claim 1 wherein the chisel tip is calotte-shaped, conical or bevelled.

3. Device as claimed in claim 2 wherein the suction nozzle of the suction device is positioned close to the chisel tip without touching it.

4. Device as claimed in claim 3 wherein the suction nozzle concentrically surrounds the chisel tip.

5. Device as claimed in claim 4 wherein the chisel tip contains a bore hole which represents the suction nozzle of the suction device.

6. Device as claimed in claim 5 wherein a filter is provided in the air flow of the suction device to collect the dust produced.

7. Device as claimed in claim 6 wherein an impactor is used in the suction device to collect the dust produced.

8. Device as claimed in claim 1 wherein the suction nozzle of the suction device is positioned close to the chisel tip without touching it.

9. Device as claimed in claim 1, wherein the suction nozzle concentrically surrounds the chisel tip.

10. Device as claimed in claim 1 wherein the chisel tip contains a bore hole which represents the suction nozzle of the suction device.

11. Device as claimed in claim 1 wherein a filter is provided in the air flow of the suction device to collect the dust produced.

12. Device as claimed in claim 1 wherein an impactor is used in the suction device to collect the dust produced.

13. Combination comprising several individual devices as claimed in claim 1 attachd to a common mounting with a single suction device provided to collect the dust produced.

* * * * *